(12) United States Patent
Nishizawa et al.

(10) Patent No.: US 9,182,216 B2
(45) Date of Patent: Nov. 10, 2015

(54) METHOD FOR OBSERVING PROTEIN CRYSTAL

(75) Inventors: Norihiko Nishizawa, Suita (JP); Hiroyoshi Matsumura, Suita (JP); Yuusuke Mori, Suita (JP); Shutaro Ishida, Suita (JP); Kazuyoshi Itoh, Suita (JP); Shigeru Sugiyama, Suita (JP); Hiroaki Adachi, Suita (JP); Tsuyoshi Inoue, Suita (JP); Kazufumi Takano, Suita (JP); Murakami Satoshi, Tokyo (JP)

(73) Assignee: OSAKA UNIVERSITY, Osaka (JP)

( * ) Notice: Subject to any disclaimer, the term of this patent is extended or adjusted under 35 U.S.C. 154(b) by 419 days.

(21) Appl. No.: 13/825,280

(22) PCT Filed: Sep. 20, 2011

(86) PCT No.: PCT/JP2011/071332
§ 371 (c)(1),
(2), (4) Date: Mar. 20, 2013

(87) PCT Pub. No.: WO2012/039377
PCT Pub. Date: Mar. 29, 2012

(65) Prior Publication Data
US 2013/0184445 A1 Jul. 18, 2013

(30) Foreign Application Priority Data

Sep. 22, 2010 (JP) ................................. 2010-212316

(51) Int. Cl.
| | |
|---|---|
| *G01B 9/02* | (2006.01) |
| *G01N 21/47* | (2006.01) |
| *C07K 1/30* | (2006.01) |
| *G01N 21/17* | (2006.01) |

(52) U.S. Cl.
CPC ............ *G01B 9/02091* (2013.01); *C07K 1/306* (2013.01); *G01N 21/4795* (2013.01); *G01N 2021/1787* (2013.01)

(58) Field of Classification Search
None
See application file for complete search history.

(56) References Cited

U.S. PATENT DOCUMENTS

| | | | |
|---|---|---|---|
| 2006/0081173 A1 | 4/2006 | Yoshizaki et al. | |
| 2007/0274580 A1 | 11/2007 | Ntziachristos et al. | |
| 2009/0080611 A1 | 3/2009 | Ganz et al. | |

FOREIGN PATENT DOCUMENTS

| | | |
|---|---|---|
| JP | 2004-3917 A | 1/2004 |
| JP | 2004-323336 A | 11/2004 |
| JP | 2005-9949 A | 1/2005 |
| JP | 2007-528500 A | 10/2007 |
| JP | 2007-285884 A | 11/2007 |
| JP | 2008-2815 A | 1/2008 |
| JP | 2009-115652 A | 5/2009 |
| WO | WO 2004/106598 A1 | 12/2004 |
| WO | WO 2009/015209 A1 | 1/2009 |
| WO | WO 2009/091053 A1 | 7/2009 |

OTHER PUBLICATIONS

Brief English explanation of WO-2009/091053-A1 dated Jul. 23, 2009.
Nishiura et al., "In vivo Ultrahigh-Resolution Ophthalmic Optical Coherence Tomography Using Gaussian-Shaped Supercontinuum", Japanese Journal of Applied Physics, vol. 49, 2010, pp. 012701-1-012701-6.
Snell et al., "Automated Sample Mounting and Alignment System for Biological Crystallography at a Synchrotron Source", Structure, Technical Advance, vol. 12, Apr. 2004, pp. 537-545.
Sugiyama et al., "Protein Crystallization in Agarose Gel with High Strength: Developing an Automated System for Protein Crystallographic Processes", Japanese Journal of Applied Physics, vol. 48, 2009, pp. 075502-1-075502-5.
International Search Report mailed on Dec. 20, 2011, issued in PCT/JP2011/071332.
PCT/IPEA/409—mailed on Dec. 19, 2012, issued in PCT/JP2011/071332.
PCT/ISA/237—mailed on Dec. 20, 2011, issued in PCT/JP2011/071332.

*Primary Examiner* — Suzanne M Noakes
(74) *Attorney, Agent, or Firm* — Birch, Stewart, Kolasch & Birch, LLP (57) ABSTRACT

Provided are a method for observing protein crystal, wherein the growth process of the protein crystals is nondestructively and three-dimensionally monitored on a real-time basis and the growth of the crystals is controlled at a high accuracy to thereby enable the formation of single crystals having good qualities, which comprises observing the protein crystals, said protein crystals having been produced by a crystallization method using a gel, by an OCT measurement using light emitted from an ultrawideband light source;
a method for observing protein crystals wherein the ultrawideband light source is an ultrawideband supercontinuum light source;
a method for observing protein crystals wherein the center wavelength of the light emitted from the ultrawideband supercontinuum light source is a 0.8 μm band; and
a method for observing protein crystals wherein the monitoring of the protein crystals is a monitoring by an in situ measurement.

17 Claims, 10 Drawing Sheets

METHOD FOR OBSERVING PROTEIN CRYSTAL

TECHNICAL FIELD

The present invention relates to a method for observing protein crystal for producing a good quality single crystal of a protein.

BACKGROUND ART

Now a day decoding of human genome has been completed and the steric structures of disease-related proteins as drug targets are being distinguished one after another by a proteomic study. By analysis of the steric structures of these disease-related proteins, it becomes possible to design a compound controlling the function of a protein, thus, drug discovery processes can be shortened significantly.

Therefore, competitions to analyze the steric structure of a protein more quickly and with higher precision using X-ray crystal analysis have intensified.

Accordingly, automatic X-ray diffraction measurement devices and the like have been developed. Further, synchrotron radiation is utilized, and large scale calculators have been developed. Thanks to the above and other, environments of analysis apparatuses are becoming sufficiently regulated. (For example, patent document 1, non-patent document 1).

PRIOR ART REFERENCE

Patent Document (Patent document 1) JP-A No. 2009-115652

Non-patent Document (Non-patent document 1) G. Snell et. al, "Automated Sample Mounting and Alignment System for Biological Crystallography at a Synchrotron Source", Structure, vol. 12 (2004), 537-545

SUMMARY OF THE INVENTION

Problem to be Solved by the Invention

Meanwhile, regarding provision of protein crystals to be subjected to this X-ray crystal analysis, it is hard to say that environments are sufficiently regulated under present circumstances.

That is, though it is necessary to provide a single crystal of good quality for carrying out X-ray crystal analysis with high precision, conventionally, it was impossible to distinguish a protein crystal and a salt crystal (hereinafter, described as "salt") without destruction, thus quick crystal analysis was prevented. At present, there is a method of effecting separation of the protein crystal from a salt using a reagent staining only a protein crystal. However, there remain problems of the presence of a protein crystal not stained, necessity of several hours for staining, unusability of a crystal once stained for analysis, and the like.

Conventionally, a fine crystal or a crystal in a highly turbid solution is observed using a digital microscope or a high resolution optical microscope. However, it was difficult to observe a shape along the depth direction (three-dimensional observation). Observation of a crystal in a highly turbid solution was more difficult.

Since there was no method for observing growth of a crystal in real time with high precision without destruction, control growth of a crystal cannot be controlled with high precision, thus, it was difficult to provide a single crystal of good quality. Further, there was also a problem that since a specific evaluation system for crystallizing performance was not defined, the success ratio of crystallization has remained only 20% or less and it was difficult to determine a means for producing a single crystal of good quality.

Further, since observation of a shape along the depth direction was difficult as described above, there was also a problem that a mount operation such as formation of a crystal to be subjected to analysis and the like couldn't but depend on manual works.

As described above, since conventionally there was a problem that it was impossible to three-dimensionally observe growth of a crystal in real time without destruction and to control growth of a crystal with high precision, it was difficult to provide a single crystal of good quality. Thus, it was impossible to sufficiently utilize well regulated environments of apparatuses as described above.

Because of this reason, there has been a desire for an observation technology of a protein crystal which enables production of a single crystal of good quality by three-dimensionally observing a growth process of a protein crystal by in-situ measurement in real time without destruction and by controlling growth of a crystal with high precision.

Further, an evaluation technology of a protein crystal using such an observation technology and a technology for separating a protein and a salt have been desired.

Means for Solving the Problem

The present inventors have intensively studied in view of the above-described problems and resultantly found that the above-described problems can be solved by inventions described below, leading to completion of the present invention. The claimed inventions will be explained below.

The invention according to claim 1 is a method for observing protein crystal for producing a good quality crystal of a protein, wherein protein crystal produced by a crystallization method using a gel is observed by OCT measurement measuring light emitting from an ultra-wideband light source and an interfering light generated from a scattering light of the emitting light.

The present inventors have paid attention to OCT measurement (Optical Coherence Tomography measurement) in which a tomographic image of a living organism or the like is obtained without cutting a measuring object such as living tissue or the like, as a technology of three-dimensionally observing a growth process of a protein crystal by in-situ measurement in real time without destruction.

The present inventors have thought that an ultra-high resolution image can be obtained even for a fine and highly transparent protein crystal by using an ultra-wideband light source, since the theoretical resolution of OCT is determined by the center wavelength of the light source and the bandwidth of the spectrum.

It has been found as a result of experiments that by using an ultra-wideband light source, OCT measurement with ultra-high resolution can be realized and even a protein crystal having a size of dozens of µm can be observed sufficiently.

Thus, in the invention of the present claim, by use of light emitted from an ultra-wideband light source, a growth process of protein crystal can be three-dimensionally observed in real time without destruction and based on the observed information, the growth process of the crystal can be controlled with high precision, thereby enabling production of a single crystal of good quality.

By appropriately extracting information from optical signals, a protein crystal and a salt, further, various reaction products can be distinguished, thus, a protein crystal can be definitely separated without destruction.

Further, by appropriately extracting information of optical signals, even a fine crystal and a crystal in a highly turbid solution can be three-dimensionally observed sufficiently.

Furthermore, since a system for evaluating crystallizing performance can be established based on the measurement result, it becomes possible to automate screening. Since evaluation of a shape along the depth direction of a crystal is enabled, it also becomes possible to automate a mount operation of a crystal.

In a crystallization method using a gel, when a gel is arranged in or around a crystal, the scattering optical signal can be enhanced by the gel, as a result, OCT measurement with ultra-higher resolution and higher sensitivity can be realized. Consequently growth of a crystal can be controlled with higher precision and a single crystal having higher quality can be produced.

Namely, a transparent protein crystal is preferable for correctly analyzing a protein crystal using X-ray. However, since a transparent protein crystal manifests little backscattered, it is difficult to measure its growth process. The present inventors have studied to find that visualization is made possible by enhancing a scattering optical signal and extracting a phase difference generated by a refractive index difference of a crystal.

In the case of a crystallization method using a gel, since scattering optical signal is enhanced by arranging the gel in or around a crystal, phase difference generated by a refractive index difference of a crystal can be easily extracted and thus visualization can be performed easily. Thus, growth of a transparent protein crystal can be controlled easily with high precision.

"Ultra-wideband light source" denotes a light source emitting light having a spectrum bandwidth of 50 to 1000 nm. Specifically mentioned are an ultra-wideband light-emitting diode, an ultra-wideband supercontinuum (SC) light source and the like to which single or several SLDs (superluminescent diodes) are connected.

The invention according to claim 2 is the method for observing protein crystal according to claim 1, wherein the above-described ultra-wideband light source is an ultra-wideband supercontinuum light source.

An ultra-high resolution image can be obtained by using an ultra-wideband light source as described above. For carrying out ultra-high resolution OCT measurement with higher sensitivity, it preferable to adopt supercontinuum light sources (SC light source) spreading the spectrum bandwidth over an ultra-wideband by a non-linear effect as disclosed in JP-A 2008-2815 by the present inventors. It has been found also that, among them, high-precision ultra-wideband SC light sources showing low-noise and high coherence and having a single-peaked smooth spectral shape such as a Gaussian type and the like are preferable.

Such high-precision ultra-wideband SC light sources have a too wide band in the original condition and cannot be used for usual fiber-type OCT in which the band is restricted by an optical fiber. Therefore, adapting to OCT using a fiber, for example, light sources emitting light having a spectrum bandwidth of 100 to 200 nm is used.

When such an ultra-wideband SC light source is used, ultra-high resolution measurement with high sensitivity is made possible, and additionally, highly functional measurements are made possible such as polarization-dependent measurement utilizing linear polarization, spectroscopic measurement when the band is extremely widely spread, phase difference measurement utilizing coherence, and the like. Therefore, not only a crystal can be observed but also information such as the composition of its surrounding environments, physical property and the like can be obtained.

The invention according to Claim 3 is the method for observing protein crystal according to Claim 2, wherein the center wavelength of light emitting from the above-described ultra-wideband supercontinuum light source is of 0.8 μm band.

For carrying out OCT measurement with ultra-high resolution and high sensitivity, ultra-wideband SC light having a center wavelength of 0.8 μm band is preferable. By use of ultra-wideband SC light having this wavelength, OCT measurement with ultra-high resolution and high sensitivity showing a depth resolution of 2 μm or less and a sensitivity of 110 dB or more becomes realistic.

The invention according to Claim 4 is the method for observing protein crystal according to any one of Claims 1 to 3, wherein the above-described observation for protein crystal is observation by in-situ measurement.

Since a growth process of a protein crystal can be three-dimensionally measured in real time without destruction by using an ultra-wideband light as described above, observation with high precision by in-situ measurement is made possible. By appropriately feeding back the in-situ measured information, a system for evaluating crystallizing performance can be formed based on the measured result, and screening can be automated. Further, it also becomes possible to produce a single crystal of good quality in an automated manner by suitably controlling the growth process of a crystal based on this feedback. It also becomes possible to automate a mount operation of a crystal by enabling evaluation of a shape along the depth direction of a crystal, and automation of the whole process from production of a crystal until X-ray crystal analysis can be expected.

The invention according to claim 5 is a method for evaluating protein crystal, wherein evaluation of protein crystal is carried out using the method for observing protein crystal according to any one of claims 1 to 4.

By using the method for observing protein crystal described above, ultra-high resolution measurement with high sensitivity is made possible, and additionally, highly functional measurements are made possible such as polarization-dependent measurement utilizing linear polarization, spectroscopic measurement when a band is extremely widely spread, phase difference measurement utilizing coherence, and the like. Therefore, information such as the composition of crystal-surrounding environments, physical property and the like can also be observed, and a system for evaluating crystallizing performance can be established.

The invention according to claim 6 is a method for separating a protein crystal and a salt, wherein separation of a protein crystal and a salt is carried out using the method for observing protein crystal according to any one of claims 1 to 4.

Since a protein crystal and a salt can be distinguished by appropriately extracting information from optical signals using the above-described method for observing protein crystal. Therefore, a protein crystal can be definitely separated without destruction to produce a single crystal of good quality.

The invention according to claim 7 is a method for separating a protein crystal and a salt for producing a good quality crystal of a protein, comprising
a gel liquid production step of gelling a material to be measured containing a protein and a salt to produce gel liquid,
a protein crystallization step of crystallizing the above-described protein from the above-described gel liquid,
an OCT measurement step of OCT-measuring the above-described gel liquid after the above-described protein crystallization step measuring light emitting from an ultra-wideband light source and an interfering light generated from a scattering light of the emitting light, and
a separation step of separating the above-described protein crystal and the above-described salt by extracting information from optical signals in the above-described OCT measurement.

As described above, it becomes possible to observe protein crystal with high precision by using an ultra-wideband light source. Further, by a crystallization method using a gel, it becomes possible to enhance a scattering optical signal and to observe protein crystal more easily.

In another aspect, since a salt is used together with a protein in production of gel liquid in the crystallization method using a gel, there is a possibility of generation of a crystal of a salt together with growth of a protein crystal. As a result, it is necessary to judge whether the crystal grown from gel liquid is a protein crystal or a salt crystal.

Since an ultra-wideband light source is used and further a gel is used to enhance the scattering optical signal, it is possible to easily distinguish a protein crystal and a salt by OCT measurement.

The invention according to claim 8 is the method for separating a protein crystal and a salt according to claim 7, wherein the above-described ultra-wideband light source is an ultra-wideband super continuum light source.

As described above, when an ultra-wideband SC light source is used, ultra-high resolution measurement with high sensitivity is made possible, and additionally, highly functional measurements are made possible such as phase difference measurement utilizing coherence, and the like. Therefore, a protein crystal and a salt can be separated with high precision.

The invention according to claim 9 is the method for separating a protein crystal and a salt according to claim 8, wherein the center wavelength of light emitting from the above-described ultra-wideband supercontinuum light source is of 0.8 µm band.

As described above, by use of ultra-wideband SC light having a center wavelength of 0.8 µm band, OCT measurement with ultra-high resolution and high sensitivity showing a depth resolution of 2 µm or less and a sensitivity of 110 dB or more becomes possible. Resultantly, a protein crystal and a salt can be separated with higher precision.

The above-described observation of a protein crystal is preferably carried out using an apparatus shown below.

That is, it is preferable that an OCT measurement device used in the method for observing protein crystal according to the present invention has
an ultra-wideband light source,
an optical branching means of branching the light emitted from the above-described ultra-wideband light source into a signal beam and a reference beam,
a signal beam irradiation means if irradiating the above-described protein crystal with the signal beam branched by the above-described optical branching means,
a light path length controlling means of controlling the light path length of the reference beam branched by the above-described optical branching means, and
a measurement means of measuring the fault information in the above-described protein crystal based on
the interference signal between the reference beam having a light path length changed by the above-described light path length controlling means and
the scattering light reflected by the above-described protein crystal irradiated by the above-described signal beam irradiation means.

Figure 2:
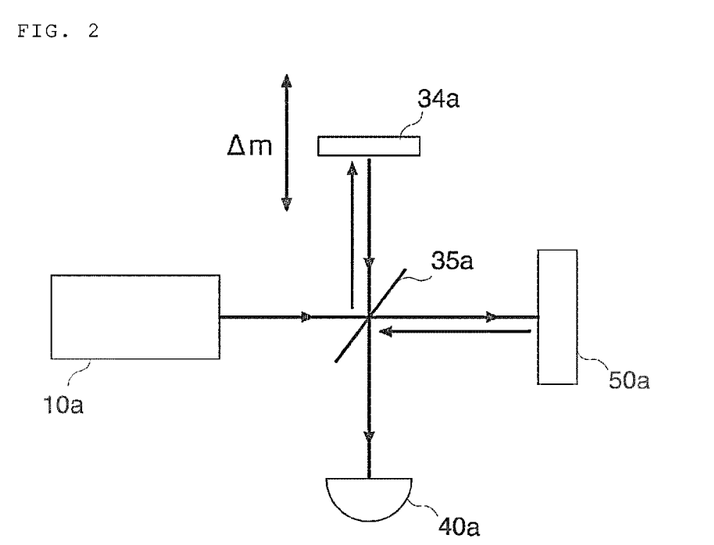
FIG. 2 is a view showing the measurement theory in OCT measurement.

A preferable OCT measurement device used for the method for observing protein crystal according to the present invention has been specifically defined above, and this will be illustrated based on FIG. 2 below. FIG. 2 shows schematically the main part of an OCT measurement device and is a view explaining the measurement theory in OCT measurement. In FIG. 2, 10a represents a light source, 34a represents a mirror for reference beam, 35a represents an optical branching instrument (beam splitter), 40a represents a photodetector and 50a represents a sample. The mirror for reference beam 34a is so designed as to move up and down (movement Δm), thereby capable of changing the light path length of the reference beam.

As shown in FIG. 2, light emitted from the light source 10a is divided by the optical branching instrument 35a into a signal beam running to the sample 50a and a reference beam running to the mirror for reference beam 34a. The signal beam running to the sample 50a is allowed to incident on the sample 50a, then, reflected to generate scattering light. In contrast, the reference beam running to the mirror for reference beam 34a is reflected by the mirror for reference beam 34a. In this state, depending on the measurement depth in the sample 50a, the mirror for reference beam 34a is moved to adjust the light path length of the reference beam. Thereafter, the generated scattering light and the reference beam having the adjusted light path length are spatially overlapped by a multiplexing means, to cause interference. This interfering light is detected by the photodetector 40a and measured. As a result, information according to the fault in a protein crystal can be measured.

The resolution ΔZ by the above-described photodetector 40 is represented by the following formula.

$$\Delta z = \frac{2\ln 2}{\pi} \frac{\lambda^2}{\Delta \lambda}$$ (Mathematical formula 1)

Here, $\lambda$ represents the center wavelength of the Gaussian spectrum and $\Delta\lambda$ represents the spectrum width thereof.

It is understood from the above-described formula that when $\Delta\lambda$ is larger (band is wider), $\Delta Z$ is smaller and higher resolution is obtained.

Figure 3:
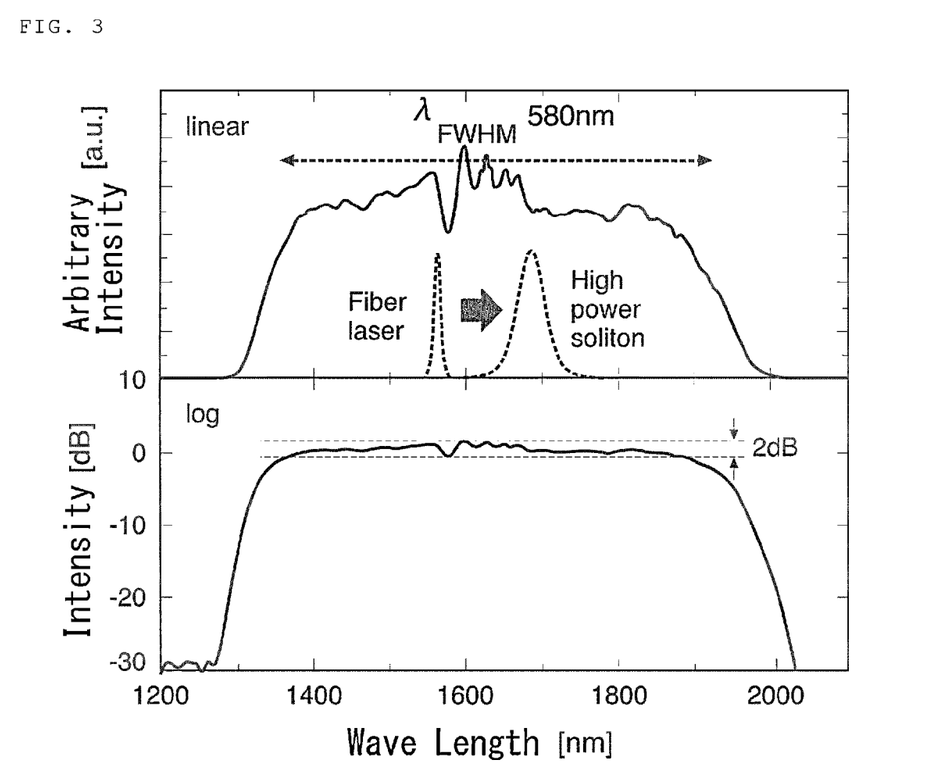
FIG. 3 is a view showing an example of the relation between the intensity and the wavelength of ultra-wideband SC light in an OCT device used in an embodiment of the present invention.

For this reason, an ultra-wideband SC light source showing a spectrum such as that shown in FIG. 3 is used as an example of a light source in the method for observing protein crystal according to the present invention. In FIG. 3, the upper view linearly represents this ultra-wideband SC light and the lower view logarithmically represents this. In both the figures, the abscissa axis represents wavelength (nm) and the ordinate axis represents intensities (a.u. and dB). As shown in FIG. 3, this ultra-wideband SC light shows flatness having an intensity of 2 dB in a wide band (band width) from a wavelength of 1300 nm to 2000 nm ($\Delta\lambda$=580 nm) showing an intensity of about 20 dB. For this reason, measurement with low-noise, high coherence and high-intensity is made possible, and even a protein crystal having a size of dozens of μm can be subjected to ultra-high resolution OCT measurement and can be three-dimensionally observed in real time without destruction.

In the above-described OCT measurement device, the above-described ultra-wideband light source is preferably an ultra-wideband supercontinuum light source.

As described above, a high resolution image can be obtained by use of ultra-wideband light sources, and among these ultra-wideband light sources, if high-precision ultra-wideband SC light sources showing low-noise and high coherence and having a single-peaked smooth spectral shape such as a Gaussian type and the like are used, ultra-high resolution measurement with high sensitivity is made possible, and additionally, highly functional measurements are made possible such as polarization-dependent measurement utilizing linear polarization, spectroscopic measurement when a band is extremely widely spread, phase difference measurement utilizing coherence, and the like. Therefore, not only crystal can be observed but also information such as the composition of its surrounding environments, physical property and the like can be observed.

It is preferable for the device of observing protein crystal used in the method for observing protein crystal according to the present invention to have the above-described OCT measurement device Because of provision of the OCT measurement device showing ultra-high resolution and high sensitivity, even a protein crystal having a size of dozens of μm can be subjected to OCT measurement with ultra-high resolution and high sensitivity, and three-dimensionally observed in real time without destruction. As a result, growth of a crystal can be controlled with higher precision and a single crystal of higher quality can be produced, thereby significantly contributing to quick and high-precision analysis of the steric structure of a protein using X-ray crystal analysis.

As described above, by use of the OCT measurement device showing ultra-high resolution and high sensitivity, OCT measurement with ultra-high resolution and high sensitivity can be carried out, and growth of a protein crystal can be three-dimensionally observed in real time without destruction. Based on the observed information, a growth process of a crystal can be controlled with high precision, as a result, a single crystal of good quality can be produced.

By use of such a protein crystal observing device, ultra-high resolution measurement with high sensitivity is made possible, and additionally, highly functional measurements are made possible such as polarization-dependent measurement utilizing linear polarization, spectroscopic measurement when a band is extremely widely spread, phase difference measurement utilizing coherence, and the like, as described above. Thus, also information such as the composition of crystal-surrounding environments, physical property and the like can be observed, and a system for evaluating crystallizing performance can be established.

By appropriately extracting information from optical signals, a protein crystal and a salt can be distinguished, thus, a protein crystal can be definitely separated without destruction and a single crystal of good quality can be produced.

Effect of the Invention

According to the present invention, a growth process of a protein crystal can be three-dimensionally observed in real time without destruction, and accordingly, growth of a crystal can be controlled with high precision and production of a single crystal of good quality is made possible.

MODES FOR CARRYING OUT THE INVENTION

The present invention will be explained based on embodiments below. The present invention is not limited to the following embodiments. It is possible to make various changes in the following embodiments, in the range identical and equivalent to the present invention.

[1] OCT Device

First, an OCT device will be illustrated. In the following descriptions, an OCT device provided with an ultra-wideband SC light generating part having an average wavelength of 1.5 μm and an OCT device provided with an ultra-wideband SC light generating part having an average wavelength of 0.8 μm are exemplified and explained.

Figure 1:
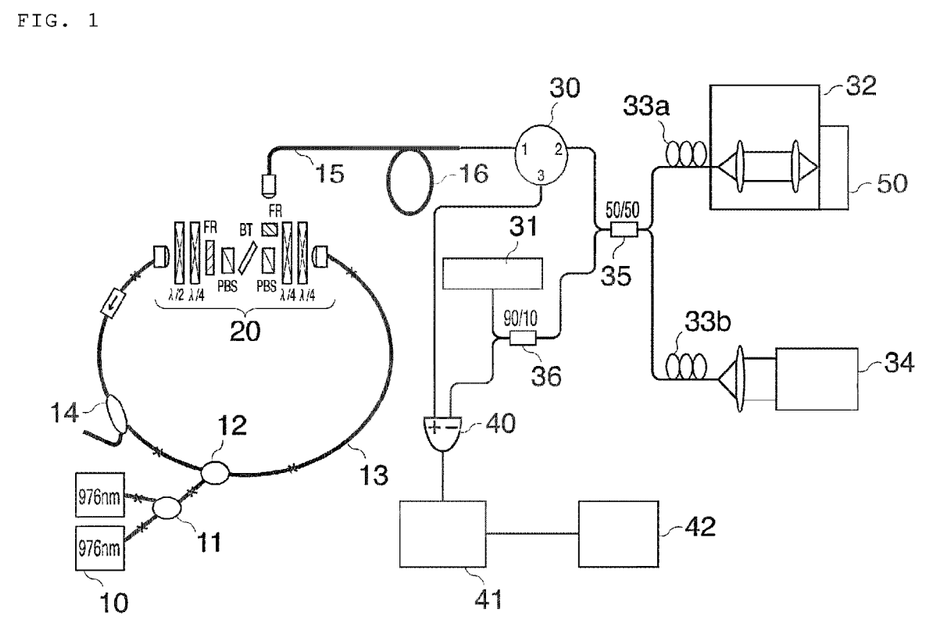
FIG. 1 is a view showing an example of the constitution of the main section of an OCT device used in an embodiment of the present invention.

1. OCT Device Provided with an Ultra-Wideband SC Light Generating Part Having an Average Wavelength of 1.5 μm FIG. 1 is a view showing the constitution of the main part of an OCT device provided with an ultra-wideband SC light generating part having an average wavelength of 1.5 μm, which is an example of an OCT device used in an embodiment of the present invention. This OCT device is roughly divided into an ultra-wideband SC light generating part represented by a heavy solid line and an observation part represented by a thin solid line.

(1) Ultra-wideband SC Light Generating Part (i) Constitution

In FIG. 1, 10 represents a semiconductor laser, 11 represents a polarized beam coupler (PBC), and 12 represents a wavelength division multi-coupler (WDM). 13 represents a high concentration erbium-added fiber (HC-EDF) (100 cm), and 14 represents a connection to an external monitor (monitor out).

15 represents a single mode fiber (SMF28), and 16 represents a normal-dispersion highly nonlinear fiber (NDHNF).

20 represents a lens system, $\lambda/2$ represents a half wave plate, $\lambda/4$ represents a ¼ wave plate, and PBS represents a polarized beam splitter. Further, FR represents a Faraday rotator, and BT represents a birefringent plate.

(ii) Function

The semiconductor laser 10 is an ultrashort pulse laser generating a laser beam having a wavelength of 976 nm. In FIG. 1, two lasers 10 are placed from the standpoint of high-power. Light having a wavelength of 976 nm is adopted since it is suitable for excitation of an erbium-added fiber.

Laser beams generated by the two semiconductor lasers 10 are polarized by PBC 11. The polarized two laser beams are multiplexed by WDM 12. The intensity of the multiplexed laser beam is increased by the high concentration erbium-added fiber 13 and transferred to the lens system 20.

Figure 4:
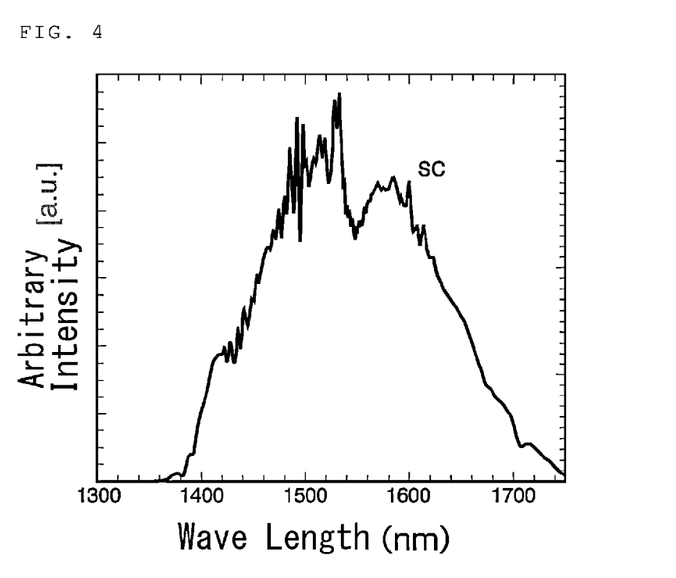
FIG. 4 is a view showing an example of the relation between the intensity and the wavelength of ultra-wideband SC light in an OCT device used in an embodiment of the present invention.

The laser beam reached to the single mode fiber 15 via the lens system 20 is, then, processed by the high concentration erbium-added fiber 16, to generate ultra-wideband SC light having the Gaussian spectrum (average wavelength: 1.5 µm) shown in FIG. 4.

(2) Observation Part (i) Constitution

In FIG. 1, 30 represents a circulator, and 31 represents an aiming light irradiation instrument (Aiming beam).

32 represents an OCT probe as a scanning irradiation light-receiving means, 34 represents a high speed scanning part (High speed scanning delay line) as a light path length regulating means, and 33a and 33b represent a polarization controller.

35 represents an optical branching instrument and multiplexer (an optical branching instrument that also serves as a multiplexer), and 36 represents an optical branching instrument. 40 represents a photodetector (Detector), and 41 represents its electronic device part (Detection electronic), connected to a computer 42. Further, 50 represent a sample to be observed.

(ii) Function

The ultra-wideband SC light generated above is transferred to the optical branching instrument and multiplexer 35 via the circulator 30, and branched at 50/50, namely, branched evenly into a signal beam and a reference beam.

The signal beam is transferred to the OCT probe 32 via the polarization controller 33a, and the reference beam is transferred to the high speed scanning part 34 via the polarization controller 33b.

The sample 50 is irradiated with the signal beam transferred to the OCT probe 32. By this signal beam irradiation, scattering light is generated from the sample 50. In irradiation, the focus position in the sample 50 can be shifted by regulating the distance between the illustrated two lenses. While, the reference beam transferred to the high speed scanning part 34 is reflected after changing the light path length.

The scattering light is received by the OCT probe 32, and transferred to the optical branching instrument and multiplexer 35 via the polarization controller 33a. While, the reference beam having the adjusted light path length is transferred to the optical branching instrument and multiplexer 35 via the polarization controller 33b.

The scattering light and the reference beam are multiplexed in the optical branching instrument and multiplexer 35, to generate interfering light. The generated interfering light is multiplexed with light from the aiming light irradiation instrument 31 at a ratio of 10:90, and transferred to the photodetector 40.

The photodetector 40 which has detected the interfering light outputs the corresponding interference signal. The interference signal is transferred to the computer 42 via the electronic device part 41, then, treated to output the positional information of the sample 50.

Figure 5:
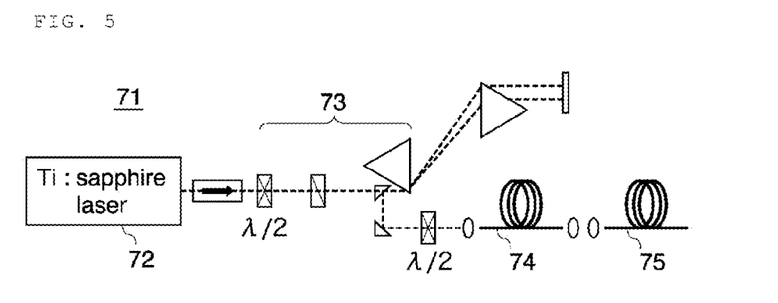
FIG. 5 is a view showing an ultra-wideband SC light generating part in another example of an OCT device used in an embodiment of the present invention.
Figure 6:
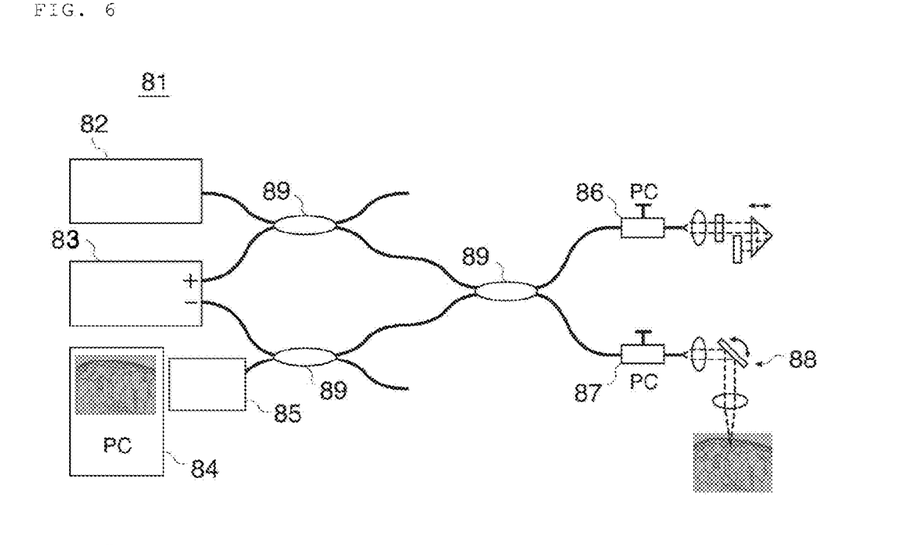
FIG. 6 is a view showing another example of an OCT device used in an embodiment of the present invention.

2. OCT Device Provided with an Ultra-Wideband SC Light Generating Part Generating a Light Having an Average Wavelength of 0.8 µm FIG. 5 is a view showing an ultra-wideband SC light generating part of an OCT device provided with an ultra-wideband SC light generating part generating a light having an average wavelength of 0.8 µm, which is another example of an OCT device used in an embodiment of the present invention. FIG. 6 is a view showing this OCT device.

Figure 7:
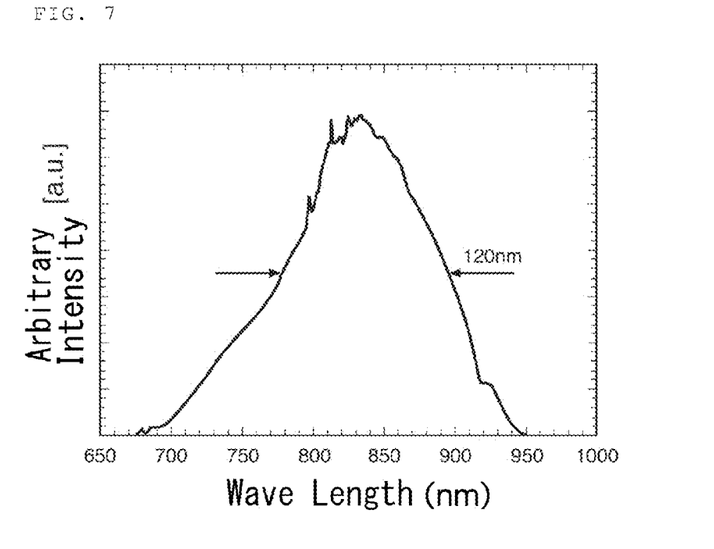
FIG. 7 is a view showing an example of the relation between the intensity and the wavelength of ultra-wideband SC light in an OCT device used in an embodiment of the present invention.

In FIG. 5, 71 represents an ultra-wideband SC light generating part, 72 represents a Ti: sapphire laser, 73 represents a polariscope, 74 represents a polarization maintaining fiber (PMF), and 75 represents a single mode fiber (SMF). In the ultra-wideband SC light generating part 71, the ultra-wideband SC light having an average wavelength of 0.8 µm shown in FIG. 7 is generated.

By use of the high-intensity ultrashort pulse laser (Ti: sapphire laser) 72 and the polarization maintaining fiber (PMF) 74 showing a property of normal dispersion, the ultra-wideband SC light generating part 71 generates high precision SC light having high intensity, low noise and Gaussian wide band, differing from general SC light having very large noise.

When a polarizer is used for output of PMF 74 in FIG. 5, linear polarized higher-precision SC light can be obtained, therefore, detection with higher precision is made possible, differing from a case of poor degree of polarization generated by ghost (extra interference signal) due to other small components crossing the main polarization component.

Figure 8:
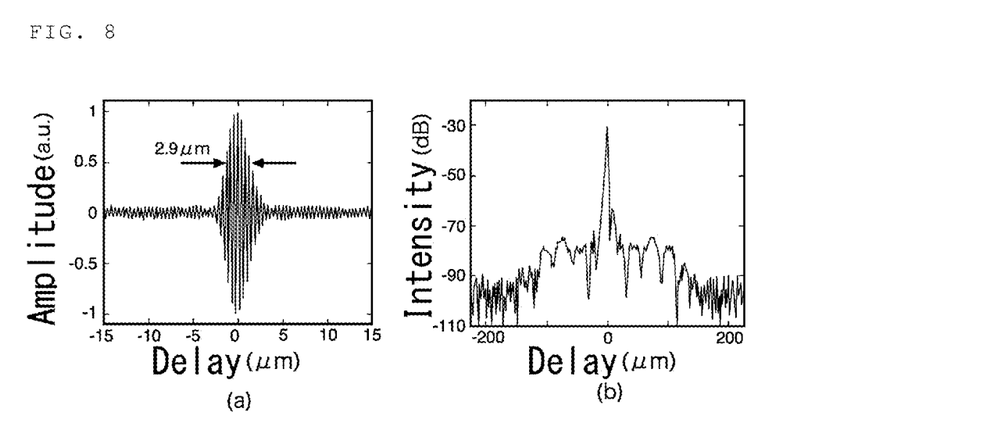
FIG. 8 is a view showing an example of an interference waveform in an embodiment of the present invention.

In FIG. 6, 81 represents an OCT device, 82 represents the ultra-wideband SC light generating part shown in FIG. 5, 83 represents a balanced detector, 84 represents a computer (PC), 85 represents an aiming light irradiation instrument, 86 and 87 represent PC for light path length regulation, 88 represents a galvano mirror (XY Galvo), and 89 represents a fiber coupler. As the fiber coupler 89, a 1:1 fiber coupler having a wider wavelength band is used, and a lens is used which compensates wavelength dispersion of a measuring system, has short focus distance and shows corrected chromatic dispersion. By use of ultra-wideband SC light having the spectrum in FIG. 7 as the light source of the OCT device shown in FIG. 6, for example, interference waveform shown in FIG. 8 is obtained. Namely, pure interference waveform including no side components is obtained, and measurement with an ultra-high resolution of 2.9 µm in air and an ultra-high resolution of 2.1 µm in a sample is made possible.

In measurement using the OCT device shown in FIG. 6, a red reference beam is superimposed with SC light and a sample is irradiated with them, and the position and arrangement of a protein crystal are observed in 3D measurement while observing the laser irradiation position by a CCD camera. In this procedure, it is also possible to observe different samples on the same plate by moving a table carrying samples under automatic control.

[2] Protein Crystal

Next, a protein crystal as a sample will be explained. In the present embodiment, a protein crystal grown in a gel is preferably used. Specifically, it is preferable that a protein is allowed to soak into a gel such as agar, or a gel and a protein are mixed and allowed to stand still, and growth of a crystal is caused under this condition.

Because of crystal growth in a gel, a lot of protein crystals having a size of 3 to 5 nm are present in a gel mesh having a size of about 300 nm, thus, intense scattering can be obtained and it becomes possible to visualize a crystal which is transparent and less-visible.

EXAMPLES

The present invention will be illustrated more specifically by examples listed below. In the following examples, the above-described OCT device provided with an ultra-wideband SC light generating part having an average wavelength of 0.8 μm was used.

Example 1

In the present example, a protein crystal grown in a gel was observed using an optical microscope and an OCT device utilizing ultra-wideband SC light as a light source, and the observation results of them were compared.

1. Crystallization Condition
(1) Preparation of Protein Solution
  Egg-white lysozyme (60 mg) was dissolved in 1.0 ml of 0.1 M sodium acetate to prepare a 60 mg/ml protein solution.
(2) Preparation of Reservoir Solution
  A sodium acetate solution (solvent: ultrapure water) having a concentration of 0.1 M was prepared (pH: 4.5), and further, sodium chloride was dissolved in this so as to have its concentration of 5.12 M to prepare a reservoir solution.
(3) Preparation of Agar Liquid (Gel)
  Agar liquid was prepared using 3 mg of agar and 50 ml of ultrapure water. Thereafter, to 400 μl of the agar liquid was added 100 μl of ultrapure water to give gel liquid.
(4) Preparation of Sodium Citrate Solution
  A sodium citrate solution having a concentration of 0.6 M (solvent: ultrapure water) was prepared.
(5) Preparation of Calcium Chloride Solution
  Calcium chloride dehydrate (132 mg) was dissolved in 1 ml of ultrapure water to prepare a calcium chloride solution having a concentration of 1.5 M.
(6) Production of Protein Crystal
  The protein solution (1 μl), the reservoir solution (1 μl), the sodium citrate solution (1 μl), the calcium chloride solution (1 μl) and the gel liquid (2 μl) were mixed, to obtain a crystal in solution having the final concentrations described below.
  protein: 10 mg/ml
  sodium chloride: 0.85 M
  sodium acetate: 0.066 M, pH4.5
  sodium citrate: 0.1 M calcium chloride: 0.25 M
  agarose gel: 1.6%
  Thereafter, the solution was allowed to stand still at 20° C., and a protein crystal was formed by a batch-wise method.
2. Observation of Crystallization
  After 72 hours, growth state of a crystal was observed using an optical microscope and an OCT device under observation conditions shown below.

Figure 9:
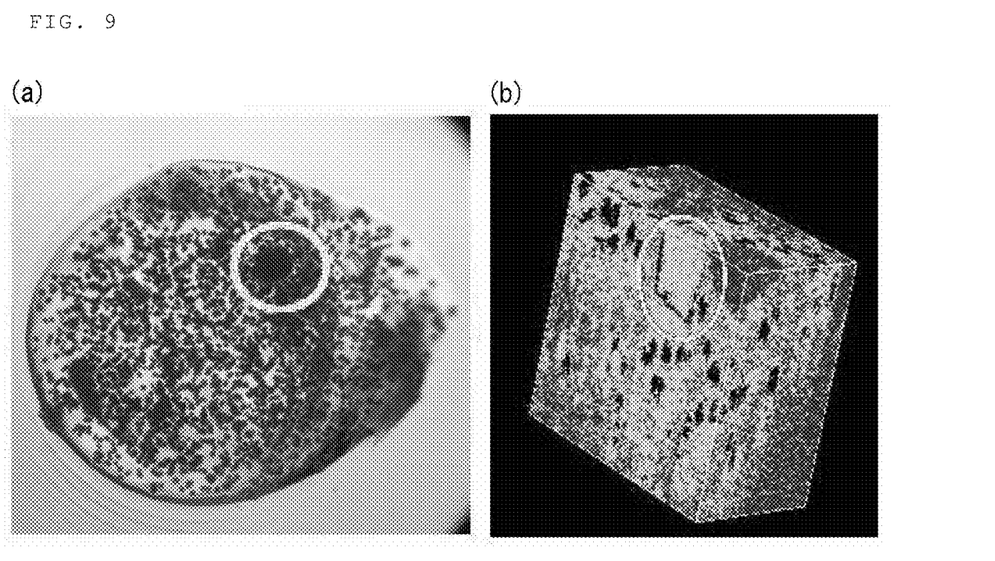
FIG. 9 shows a microscope image and an OCT image in crystal observation in Example 1 of the present invention.

(1) Observation Condition
(i). Microscopic Observation
  optical microscope: Nikon SMZ1000
  light source: white light
(ii). OCT Observation
  light source: 810 nm centered SC light, bandwidth: 134 nm
  measurement sensitivity: 100 dB
  optical intensity: SC output: 350 mW, interferometer input: 30 mW
  resolution: in air: 2.9 μm, in sample: 2.0 μm
  observation region: lateral size 2 mm×longitudinal size 2 mm×height 1 mm (three-dimension)
  pixel number: lateral direction 250×longitudinal direction 250×height direction 1000 (three-dimension)
(2) Observation Result
  The observation results are shown in FIG. 9. In FIG. 9, (a) represents a microscope image, and (b) represents an OCT image. Though a protein crystal is present in a precipitate (position indicated by circular mark), it is difficult to confirm the presence of a crystal in a microscope image as shown in FIG. 9(a). While, in an OCT image, a crystal of lysozyme can be definitely confirmed as shown in FIG. 9(b).

Example 2

In the present example, a sample containing a protein crystal and a low molecular salt was prepared, and the observation results with an optical microscope and with an OCT device were compared.

1. Crystallization Condition
(1) Preparation of Protein Solution
  Egg-white lysozyme (72 mg) was dissolved in 1.0 ml of 0.1 M sodium acetate to prepare a 72 mg/ml protein solution.
(2) Preparation of Reservoir Solution
  A sodium acetate solution (solvent: ultrapure water) having a concentration of 0.1 M was prepared (pH: 4.5), and further, sodium chloride was dissolved in this so as to have its concentration of 5.12 M to prepare a reservoir solution.
(3) Preparation of Agar Liquid (Gel)
  Agar liquid was prepared using 3 mg of agar and 50 ml of ultrapure water. The agar liquid was used as gel liquid.
(4) Preparation of Potassium Phosphate Solution
  A potassium phosphate solution sodium having a concentration of 0.6 M (solvent: ultrapure water) was prepared (pH7.5).
(5) Preparation of Calcium Chloride Solution
  Calcium chloride dehydrate (22 mg) was dissolved in 1 ml of ultrapure water to prepare a calcium chloride solution having a concentration of 0.15 M.
(6) Production of Protein Crystal
  The protein solution (1 μl), the reservoir solution (1 μl), the potassium phosphate solution (1 μl), the calcium chloride solution (1 μl) and the gel liquid (2 μl) were mixed, to obtain a crystal in solution having the final concentrations described below.
  protein: 12 mg/ml
  sodium chloride: 0.85 M
  sodium acetate: 0.066 M, pH4.5
  potassium phosphate: 0.1 M, pH7.5
  calcium chloride: 0.05 M
  agarose gel: 2%
  Thereafter, the solution was allowed to stand still at 20° C., and a protein crystal was formed by a batch-wise method.
2. Observation of Crystallization
  After 72 hours, a microscopic observation and an OCT observation were carried out according to the same observation conditions as those in Example 1, except that, in the OCT observation, the observation region (Cross section) was "lateral size 2 mm×height 0.5 mm" and the pixel number was "lateral direction 250×height direction 500".

(2) Observation Result

Figure 10:
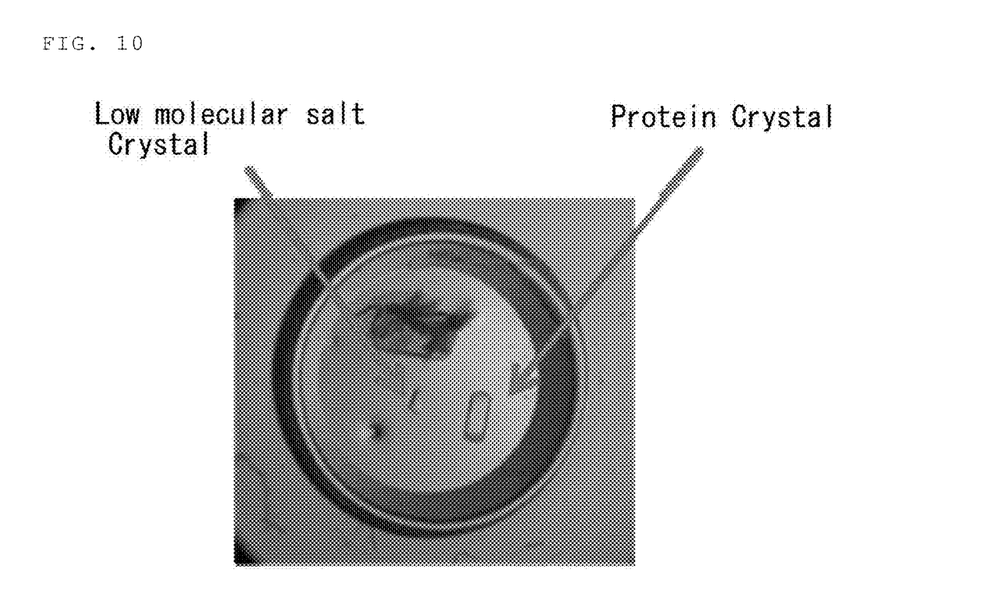
FIG. 10 shows microscope images in crystal observation in Example 2 of the present invention.
Figure 11:
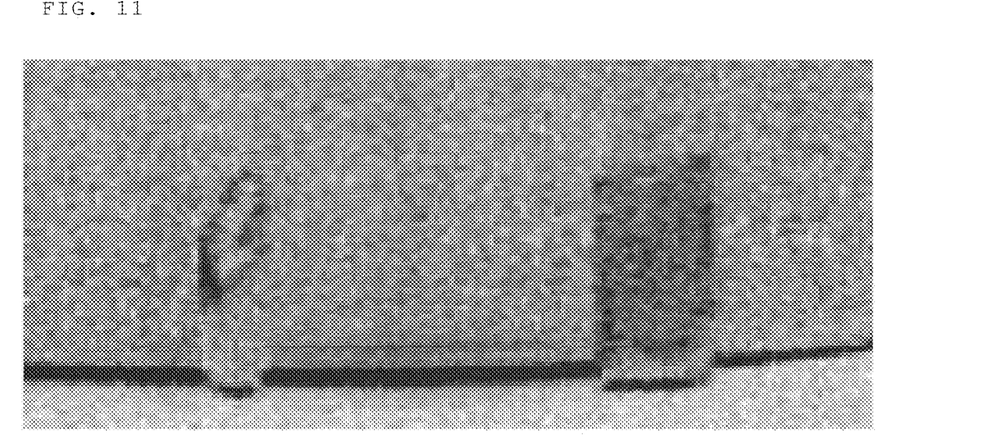
FIG. 11 is a view showing an OCT image in crystal observation in Example 2 of the present invention.

The observation result with a microscope is shown in FIG. 10, and the observation result with OCT is shown in FIG. 11. In FIGS. 10 and 11, the low molecular salt crystal to the left is potassium phosphate and the protein crystal to the right is crystal of lysozyme. As shown in FIG. 10, in the microscope image, both of them are transparent and it is difficult to distinguish them. While, in the OCT image, definite differences in form and signal strength of them can be observed and they can be distinguished.

Example 3

In the present example, the state of crystal growth in a gel was observed regarding an Egg-white lysozyme crystal as a protein crystal while changing gel concentration.

1. Crystallization Condition (1) Preparation of Protein Solution

Egg-white lysozyme (150 mg) was dissolved in 1.0 ml of 0.1 M sodium acetate to prepare a 150 mg/ml protein solution.

(2) Preparation of Reservoir Solution

A sodium acetate solution (solvent: ultrapure water) having a concentration of 0.1 M was prepared (pH: 4.5), and further, sodium chloride was dissolved in this so as to have its concentration of 1.53 M to prepare a reservoir solution.

(3) Preparation of Agar Liquid (Gel)

Agar liquid was prepared using 3 mg of agar and 50 ml of ultrapure water. Thereafter, to 450 µl of the agar liquid was added 50 µl of ultrapure water to give gel liquid.

(4) Production of Protein Crystal

The gel liquid (2 µl), the protein solution (2 µl) and the reservoir solution (2 µl) were mixed, to obtain a crystal in solution having the final concentrations: 50 mg/ml of protein, 0.51 M of sodium chloride and 1.8% of agarose gel. Thereafter, the solution was allowed to stand still at 20° C., and a protein crystal was formed by a batch-wise method.

2. Observation of Crystallization

After 72 hours, an OCT observation was carried out.

(1) Observation Conditions light source: 810 nm centered SC light, bandwidth: 134 nm measurement sensitivity: 100 dB optical intensity: SC output: 350 mW, interferometer input: 30 mW Under the above observation conditions, growth state of a crystal in a gel was observed while monitoring the positions of the crystal and the irradiation light using a CCD camera.

(2) Observation Result

Figure 12:
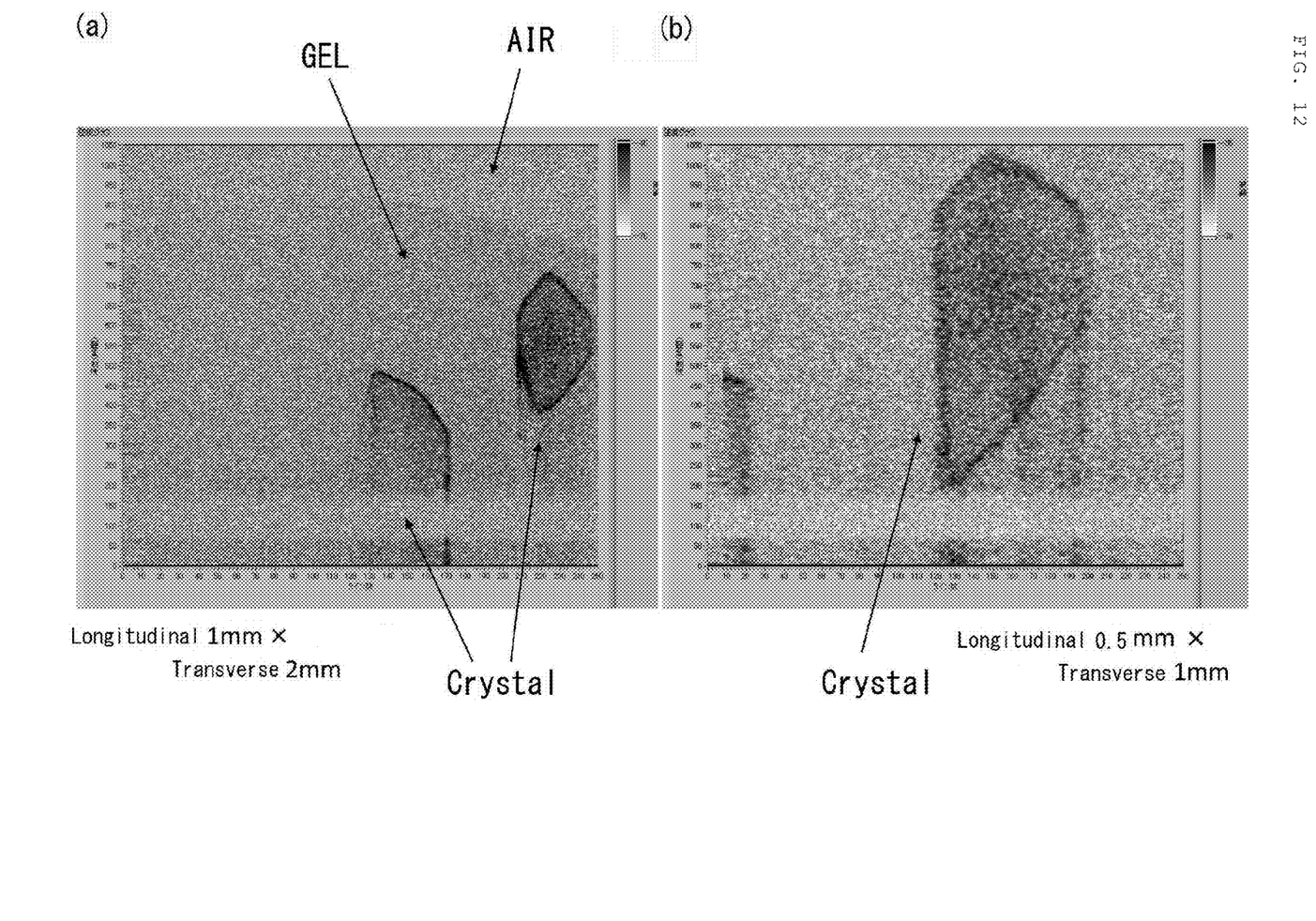
FIG. 12 is a view showing an OCT image of a crystal of a protein in Example 3 of the present invention.
Figure 13:
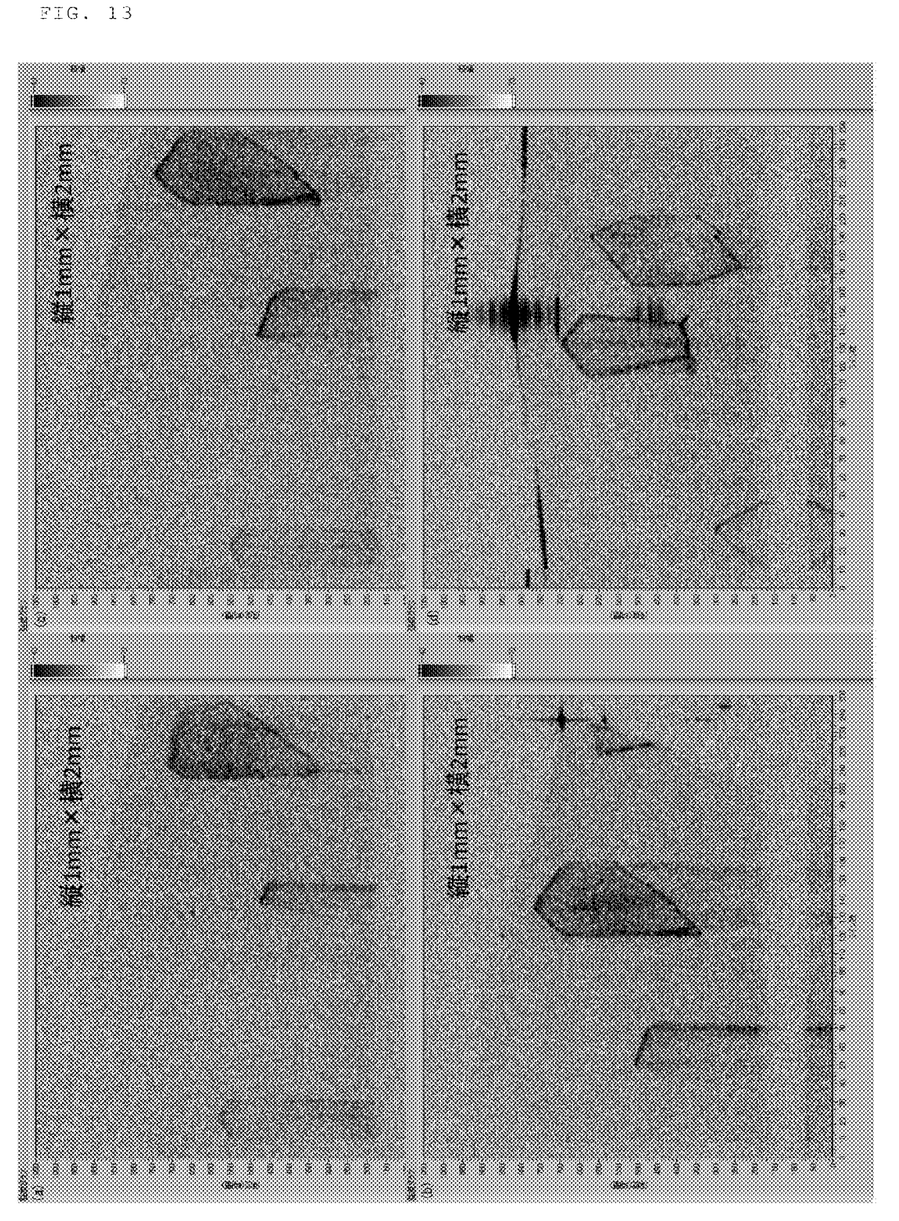
FIG. 13 is a view showing an OCT image of a crystal of a protein in Example 3 of the present invention.

The observation results with OCT are shown in FIGS. 12 and 13. In FIGS. 12 and 13, the abscissa axis represents the Lateral position and the ordinate axis represents the vertical position. The sighs (a) and (b) in FIG. 12 and the sighs (a)-(d) in FIG. 13 represent lysozyme crystals grown in 1.8% agarose gel. They are measured results regarding the same sample but in different measurement positions. By combining these two dimensional images, a three dimensional images can be made.

It is understood that by using OCT measurement, a crystal of a protein can be distinguished clearly from a gel and air.

Example 4

In the present example, the state of crystal growth in a gel was observed regarding a lysozyme crystal as a protein crystal while changing gel material.

1. Crystallization Condition protein solution: 50 mg/ml lysozyme reservoir solution:

0.1 M sodium acetate (pH:4.5)

0.51 M sodium chloride gel liquid:

Agarose IX-A (manufactured by SIGMA) (3 g) was prepared with 50 ml of ultrapure water, to give a 6% gel liquid. This liquid was gelled once, then, melted again. The melted liquid was diluted 6-times and 3-times with ultrapure water, to obtain 1% gel liquid and 2% gel liquid, respectively.

The resultant gel (2 µl) was added to a drop part of a plate for crystallization, and solidified. Then, a mixed solution of the above-described protein solution (2 µl) and the reservoir solution (2 µl) was laminated on the solidified gel. Next, 100 µl of the reservoir solution was added to the reservoir part and allowed to stand still at 20° C., and a protein crystal was formed by a sitting drop vapor diffusion method 2. Observation of Crystallization After 120 hours, OCT measurement was carried out using each of the mixed liquids.

(1) Observation Condition

The same observation conditions as those in Example 3 were used.

(2) Observation Results

Figure 14:
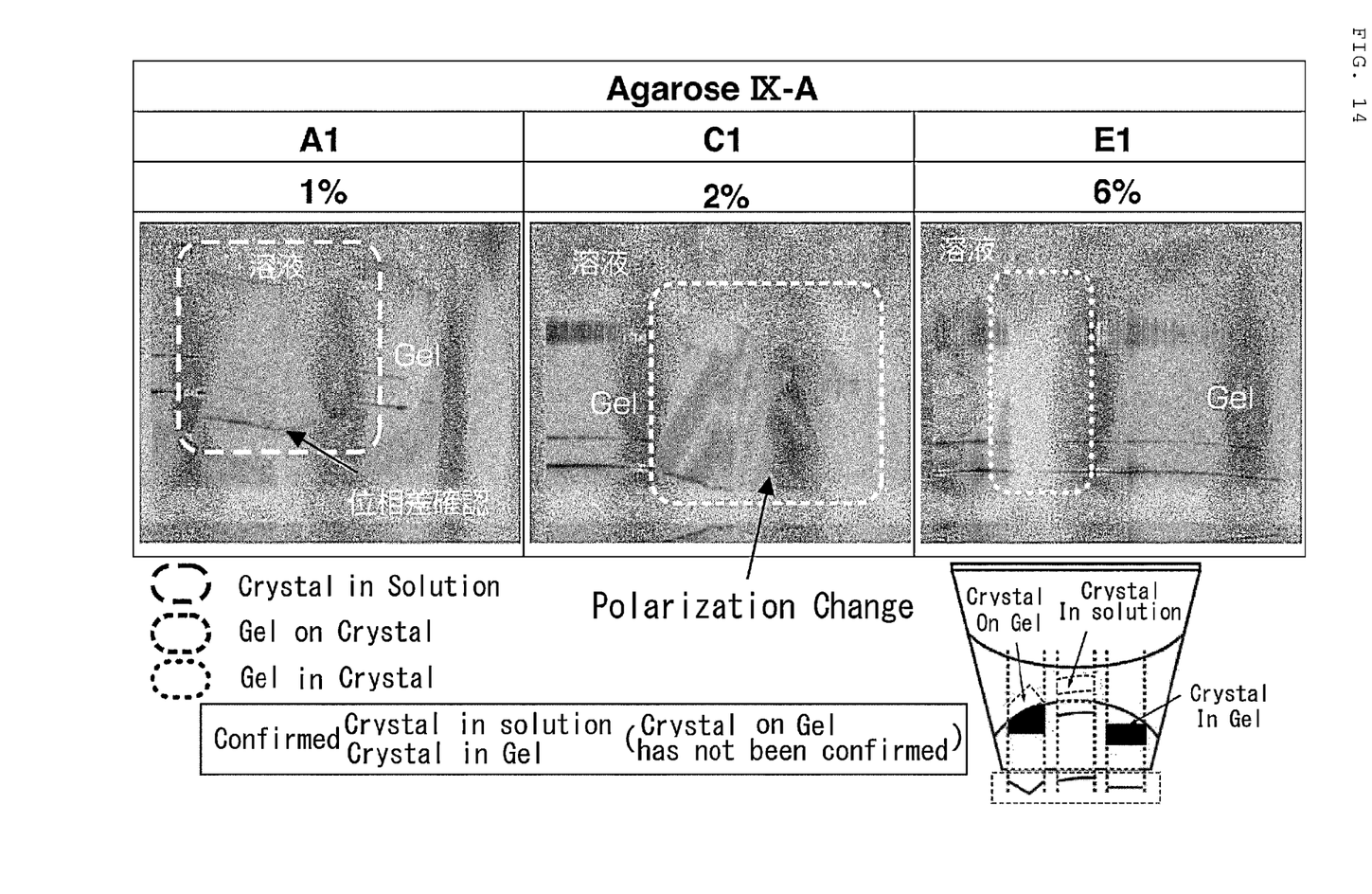
FIG. 14 is a view showing an OCT image of a crystal of a protein in Example 4 of the present invention.

The observation results (OCT images) are shown in FIG. 14. In FIG. 14, A1, C1 and E1 represent the drop number of a plate, and 1%, 2% and 6% are the final gel concentrations. As shown in FIG. 14, when a protein crystal is present in a solution, generation of phase difference can be confirmed in an OCT image, thus, the presence of a protein crystal can be confirmed. Since this phase difference is visible because of generation of scattering in the shape of a crystal, it is understood that the protein crystal has a flat shape.

When a protein crystal is present in a gel or when a protein crystal is present on a gel, change of polarization can be confirmed in an OCT image, thus, the presence of a protein crystal can be confirmed.

It was verified from the above-described results that by selecting a gel material, growth of any crystal formed in a solution, on a gel or in a gel can be observed, and the states around the crystal can also be confirmed. In the present example, it could be confirmed that the above-described observation can be carried out irrespective of turbidity of gel liquid.

Example 5

In the present example, the state of crystal growth in a gel was observed regarding a crystal of phosphoribulokinase (PRK) derived from synechococcus as a protein crystal while changing gel material.

1. Crystallization Condition protein solution: 20 mg/ml PRK reservoir solution:

0.1 M MES-KOH (pH:6.5)

10% (w/v) Isopropanol 0.2 M potassium acetate gel liquid:

Agarose SeaKem (manufactured by Lonza) (3 g) was prepared with 50 ml of ultrapure water, to give a 6% gel liquid.

This liquid was gelled once, then, melted again. The melted liquid was diluted 6-times, 3-times and 1.5-times with ultrapure water, to obtain 1% gel liquid, 2% gel liquid and 4% gel liquid, respectively.

Except for using this gel liquid, a protein crystal was formed according to the same method as that in Example 4.

2. Observation of Crystallization After 120 hours, OCT measurement was carried out using each of the mixed liquids.

(1) Observation Condition

The same observation conditions as those in Example 3 were used.

(2) Observation Results

Figure 15:
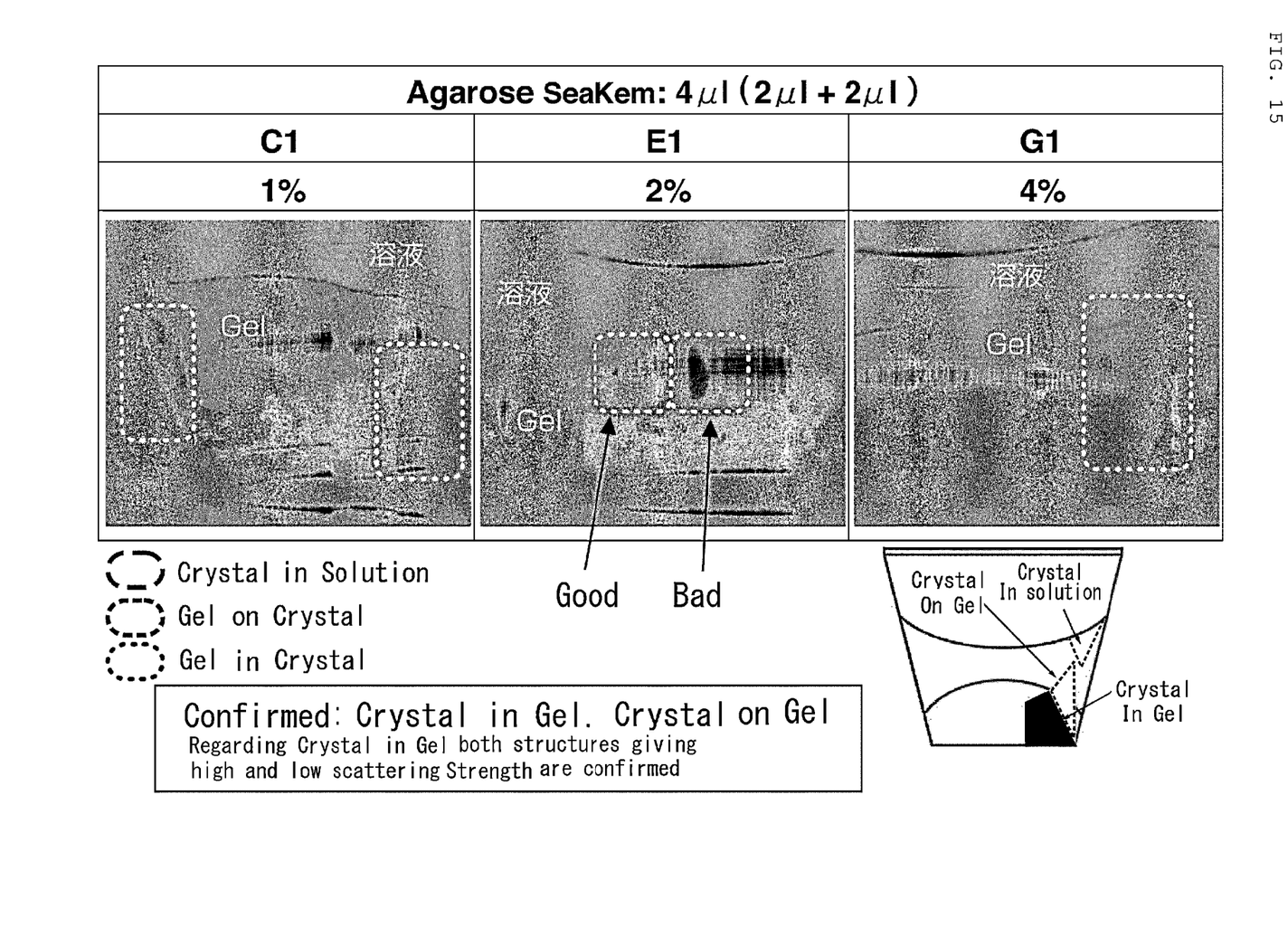
FIG. 15 is a view showing an OCT image of a crystal of a protein in Example 5 of the present invention.

The observation results (OCT images) are shown in FIG. 15.

In FIG. 15, C1, E1 and G1 represent the drop number of a plate, and 1%, 2% and 4% are the final gel concentrations. In FIG. 15, "4 μl (2 μl+2 μl)" means that 2 μl of reservoir solution is added to 2 μl of protein solution in the mixed solution, and the total of the solution is 4 μl. As shown in FIG. 15, growth of any crystal formed in a solution, on a gel or in a gel can be observed, same as in Example 4. In the present example also, it could be confirmed that the above-described observation can be carried out irrespective of turbidity of gel liquid.

In the center figure of FIG. 15, the presence of two protein crystals can be confirmed, and it is understood that one (left side) has good crystallinity and the other (right side) has poor crystallinity, depending on a difference in its scattering intensity. In the present example, crystallinity can be evaluated depending on a difference in scattering intensity.

Example 6 and Comparative Example

In the present example, the state of crystal growth in a gel was observed regarding a crystal of PRK as a protein crystal using a gel material different from those used in Examples 4 and 5. In the comparative example, the observation was carried out using optical micro scope.

1. Crystallization Condition

The same protein solution and reservoir solution were used as those used in Example 5. Agarose SeaPlaque (manufactured by Lonza) (3 g) was prepared with 50 ml of ultrapure water to give a gel liquid.

The above-described protein solution (2 μl) and the reservoir solution (2 μl) were mixed, and the mixed solution thus obtained was added to a drop part of a plate for crystallization to obtain a crystal in solution. Next, 100 μl of the reservoir solution was added to the reservoir part and allowed to stand still at 20° C., and a protein crystal was formed by a sitting drop vapor diffusion method 2. Observation of Crystallization After 120 hours, OCT measurement was carried out.

(1) Observation Condition

The same observation conditions as those in Example 3 were used.

As a comparative example, the same sample was observed with an optical micro scope.

(2) Observation Results

Figure 16:
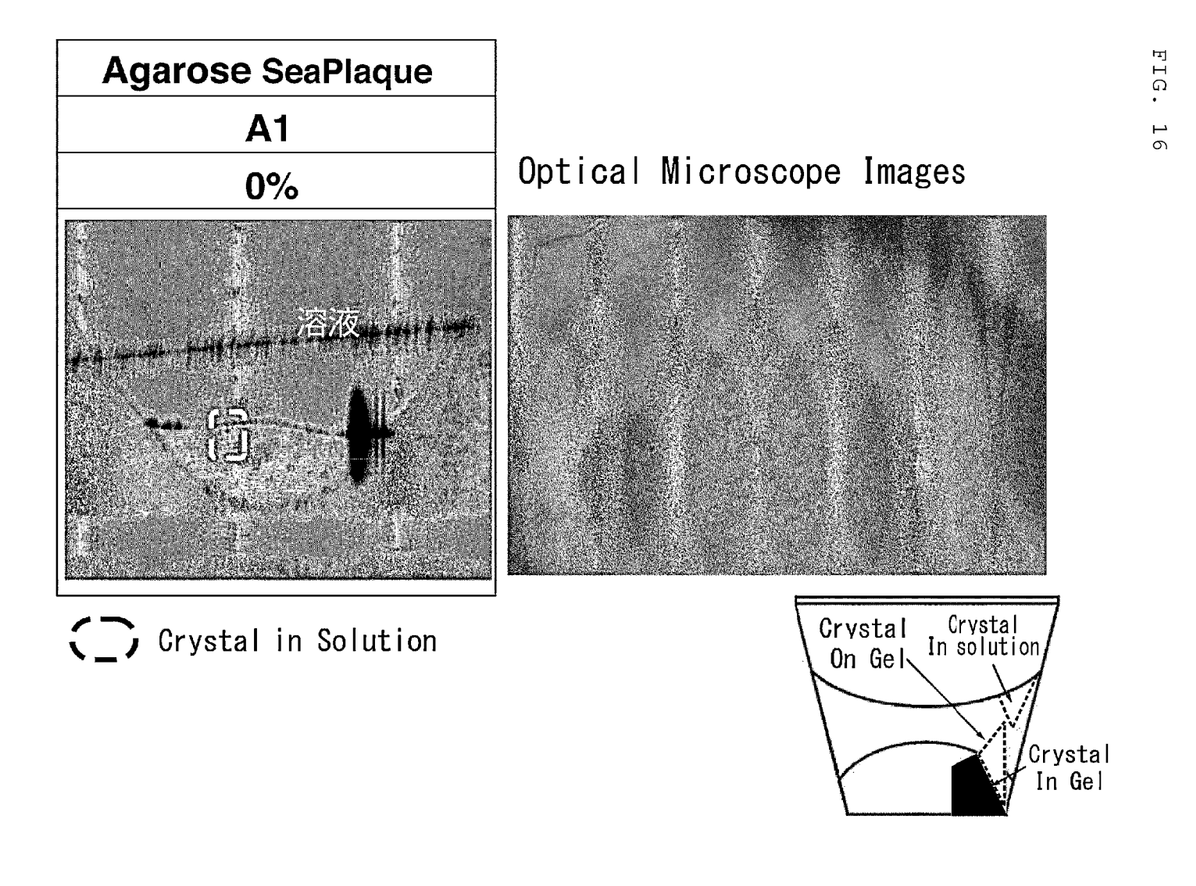
FIG. 16 is a view showing an OCT image of a crystal of a protein in Example 6 of the present invention.

The observation results (OCT images) are shown in FIG. 16. In FIG. 16, A1 represent the drop number of a plate, and 0% is the final gel concentrations. As shown in FIG. 16, the presence of a protein crystal in the solution can be confirmed by an observation with OCT. While, with an optical microscope, growth of a crystal cannot be confirmed, and only its surface can be observed due to weak scattering light.

As explained above, a protein crystal can be in-situ observed with high resolution in real time without destruction, according to the present invention. Further, a protein crystal in a highly turbid sample can be observed. Moreover, the three-dimensional structure and the three-dimensional distribution of a crystal, the positional relation of a crystal and a gel phase and a liquid phase, discrimination of a salt and a protein crystal and of an imperfect crystal (amorphous) and a perfect crystal, determination of three-dimensional arrangement, precipitation, aggregation and the like can be observed. Further, distribution of a gel incorporated in a crystal can be observed.

REFERENCE NUMERALS 10 semiconductor laser
10a light source
11 polarized beam coupler (PBC)
12 wavelength division multi-coupler (WDM)
13 high concentration erbium-doped fiber (HC-EDF)
14 connection to an external monitor
15, 75 single mode fiber (SMF28)
16 normal-dispersion highly nonlinear fiber (NDHNF)
20 lens system
30 circulator
31, 85 aiming light irradiation instrument
32 OCT probe
33a, 33b polarization controller
34 high speed scanning part
34a mirror for reference beam
35 optical branching instrument and multiplexer
35a optical branching instrument (beam splitter)
36 optical branching instrument
40, 40a photodetector
41 electronic device part
42, 84 computer
50, 50a sample to be observed
71, 82 ultra-wideband SC light generating part
72 Ti: sapphire laser
73 polariscope
74 polarization maintaining fiber (PMF)
83 balanced detector
86, 87 PC for light path length regulation
88 galvano mirror (XY Galvo)
89 fiber coupler

What is claimed is:

1. A method for observing a good quality protein crystal, wherein said protein crystal is produced by a gel crystallization method and said protein crystal is observed by optical coherence tomography (OCT) and measuring light emitting from an ultra-wideband light source and an interfering light generated from a scattering light of the emitting light.

2. The method according to claim 1, wherein said ultra-wideband light source is an ultra-wideband supercontinuum light source.

3. The method according to claim 2, wherein the center wavelength of light emitting from said ultra-wideband supercontinuum light source is a 0.8 μm band.

4. The method according to claim 1, wherein said protein crystal is observation takes place by in-situ measurement.

5. A method for evaluating the quality of a protein crystal, wherein said evaluation is carried out using the method according to claim 1.

6. A method for distinguishing a protein crystal from a salt crystal, wherein said protein crystal and said salt crystal are distinguished from one another by performing the method according to claim 1.

7. A method for distinguishing a good quality protein crystal from a salt crystal comprising producing a liquid-gel crystallization composition comprising a gel, a protein to be crystallized and a buffer containing at least one salt, crystallizing said protein by placing said crystallization composition under conditions which promotes crystallization of said protein in the liquid-gel such that a protein crystal and a salt crystal are produced, performing an optical coherence tomography (OCT) measurement step on said liquid-gel liquid containing said protein crystal and said salt crystal by measuring light emitting from an ultra-wideband light source and an interfering light generated from a scattering light of the emitting light, and distinguishing said protein crystal from said salt crystal by extracting information from optical signals in the OCT measurement.

8. The method according to claim 7, wherein the said ultra-wideband light source is an ultra-wideband super continuum light source.

9. The method according to claim 8, wherein the center wavelength of light emitting from the said ultra-wideband supercontinuum light source is of 0.8 μm band.

10. The method according to claim 2, wherein the above-described observation for protein crystal is observation by in-situ measurement.

11. The method according to claim 3, wherein the above-described observation for protein crystal is observation by in-situ measurement.

12. A method for evaluating the quality of a protein crystal, wherein said evaluation is carried out using the method according to claim 2.

13. A method for evaluating the quality of a protein crystal, wherein said evaluation is carried out using the method according to claim 3.

14. A method for evaluating the quality of a protein crystal, wherein said evaluation is carried out using the method according to claim 4.

15. A method for distinguishing a protein crystal from a salt crystal, wherein said protein crystal and said salt crystal are distinguished from one another by performing the method according to claim 2.

16. A method for distinguishing a protein crystal from a salt crystal, wherein said protein crystal and said salt crystal are distinguished from one another by performing the method according to claim 3.

17. A method for distinguishing a protein crystal from a salt crystal, wherein said protein crystal and said salt crystal are distinguished from one another by performing the method according to claim 4.

* * * * *